United States Patent [19]

Summerlin

[11] Patent Number: 5,237,104

[45] Date of Patent: Aug. 17, 1993

[54] COBALT CATALYST RECOVERY USING HEAVY OLEFIN ABSORBENT

[75] Inventor: William H. Summerlin, Baton Rouge, La.

[73] Assignee: Exxon Chemical Patents Inc., Linden, N.J.

[21] Appl. No.: 891,317

[22] Filed: May 29, 1992

[51] Int. Cl.$^5$ ............................................. C07C 45/50
[52] U.S. Cl. ................................... 568/451; 568/452; 568/454
[58] Field of Search ............... 568/451, 454, 455, 492

[56] References Cited

U.S. PATENT DOCUMENTS

| | | | |
|---|---|---|---|
| 2,744,921 | 5/1956 | Mertzweiller et al. | 260/414 |
| 2,816,933 | 12/1957 | Mertzweiler | 260/638 |
| 3,520,937 | 7/1970 | Moell et al. | 260/604 |
| 3,725,534 | 4/1973 | Reisch | 423/417 |
| 3,868,422 | 2/1975 | Hart et al. | 260/604 HF |
| 3,941,848 | 3/1976 | Kummer et al. | 260/604 HF |
| 4,390,473 | 6/1983 | Cooper | 260/429 R |
| 4,625,067 | 11/1986 | Hanin | 568/451 |
| 5,091,599 | 2/1992 | DeMunck et al. | 568/882 |

FOREIGN PATENT DOCUMENTS 0011842 6/1980 European Pat. Off. .
0391650 10/1990 European Pat. Off. .

Primary Examiner—Werren B. Lone

[57] ABSTRACT

An olefin of a heavier molecular weight than the feed olefin in a hydroformylation reaction process is used as an absorbent for recovering hydro cobalt carbonyl stripped from an oxonation reactor product. The cobalt in the stripping gas is completely absorbed but light hydrocarbons, e.g., hydrocarbons having a carbon number of $C_7$ or less, are only partially absorbed, thus permitting hydro cobalt carbonyl to be recycled to the oxonation reactor without a continuing concentration build up of light hydrocarbons, e.g., paraffins.

21 Claims, 2 Drawing Sheets

COBALT CATALYST RECOVERY USING HEAVY OLEFIN ABSORBENT

The present invention relates generally to a method of removing dissolved cobalt compounds from the products of a cobalt catalyzed hydroformylation reaction. This method is particularly useful in removing dissolved cobalt from crude products formed from olefinic feedstocks having a carbon number in the range from about $C_4$ to about $C_7$.

BACKGROUND OF THE INVENTION

Hydroformylation reactions involve the preparation of oxygenated organic compounds by the reaction of carbon monoxide and hydrogen (i.e., syn or synthesis gas) with carbon compounds containing olefinic unsaturation. The reaction is performed in the presence of a carbonylation catalyst and results in the formation of a compound, for example an aldehyde, which has one more carbon atom in its molecular structure than the starting olefinic feedstock.

By way of example, higher alcohols may be produced in the so-called "oxo" process by hydroformylation of commercial $C_4$ to $C_{16}$ olefin fractions to an aldehyde-containing oxonation product, which on hydrogenation yields respective $C_5$ to $C_{17}$ saturated alcohols. The olefin feedstocks react to form aldehydes, alcohols, formate esters and some higher boiling condensation, esterification, and dehydration by-products. Some of the olefin feedstock is also hydrogenated to form paraffins.

The catalyst normally employed is a homogeneous cobalt catalyst, hydro cobalt tetracarbonyl, i.e., $HCo(CO)_4$. The hydroformylation reactors operate typically at 120°-180° C. and at a pressure of 202.6-303.9 bar. At these conditions the cobalt is almost entirely in the form of hydro cobalt tetracarbonyl.

Prior to sending the hydroformylation product to the next processing step which is normally hydrogenation where the aldehydes are converted to the corresponding alcohols the cobalt catalyst must be removed. One such conventional method for removing cobalt values from a crude product is by a technique commonly referred to as "Cobalt Flash." U.S. Pat. No. 4,625,067 (Hanin), which issued on Nov. 25, 1986, discloses the Cobalt Flash process wherein the crude product is contacted with a stream of stripping gas to entrain volatile cobalt compounds. The contacting is performed in the presence of water and aqueous acid to dissolve those cobalt values not entrained in the gas under the conditions of temperature and pressure employed for the contacting, and the aqueous phase is subsequently separated from the organic hydroformylation reaction product.

Although the stripping method disclosed in the Hanin patent overcomes the disposal and chemical additive costs of the caustic/acidification method disclosed in U.S. Pat. No. 3,725,534 (Reisch), which issued on Apr. 3, 1973, and U.S. Pat. No. 5,091,599 (DeMunck et al.), which issued on Feb. 25, 1992, it has the disadvantage that when lower carbon number olefins (e.g., $C_7$ and below) are used as feedstock, unreacted compounds such as olefins and/or paraffins are stripped out together with the volatile cobalt compounds. These olefins and/or paraffins are then absorbed into the olefinic feedstock and recycled to the oxo reactor. This occurs because lower carbon number feedstocks such as heptene have roughly the same volatility as the cobalt specie, thereby causing it to be entrained together with the volatile cobalt and taken out overhead. At atmospheric pressure the boiling point of hydro cobalt carbonyl is estimated to be 47° C. which falls between the boiling points of n-pentane, i.e., 36° C., and n-hexane, i.e., 69° C. As a result when the hydro cobalt tetracarbonyl is stripped at 95° C. and less than 10 atmospheres, as described in U.S. Pat. No. 4,625,067, the light hydrocarbons present are also taken overhead in significant quantities.

In the absorption step of Hanin, the oxo feed olefin is used as the absorbent and has the same carbon number as the stripped paraffins and olefins. As such the stripped paraffins and olefins are absorbed into the feed olefin along with the hydro cobalt tetracarbonyl, i.e., volatile cobalt carbonyl. As the oxo cycle is repeated the light hydrocarbon level in the oxonation feed rapidly increases, thus sharply decreasing the olefin content of the feed and reducing net olefin feed rates.

The present inventor has developed a novel method of recovering cobalt values by means of the Cobalt Flash mode which does not cause the build up of unreacted light hydrocarbons within the system, thereby avoiding a decrease in the net olefin feed rate. This is accomplished by replacing the olefinic feed in the absorber with a heavier molecular weight higher olefin to serve as the absorbent. Use of the heavy olefin absorbent accomplishes two primary objectives. First, the total amount of paraffin which can be absorbed is smaller. Second, the higher gas to olefin ratio will heat up the olefins as they are countercurrently contacted also decreasing the total amount of paraffin which will be absorbed, and accelerating the complexation of the cobalt with heavier olefin as the temperature increases. Therefore, a majority of the paraffins and other light hydrocarbons remain in the gas stream and exit the absorber.

Although U.S. Pat. No. 5,091,599 (DeMunc al.) is not directed to a Cobalt Flash method, it does incorporate in its caustic/acidification method a step wherein the volatile cobalt from a stripper reactor is contacted with an absorbent other than the olefinic feed to recycle the cobalt catalyst back to oxonation of $C_3$ to $C_6$ olefins. Traditionally the absorbent used in caustic/acidification method is the olefinic feedstock. DeMunck et al. replaces the olefinic feedstock with the residue obtained during hydroformylation. DeMunck et al. discovered that the so called U.HOF, the product left after upgrading of the heavy oxo by-products is a very effective hydro cobalt carbonyl absorption fluid, almost comparable to olefin feed and much better than the heavy oxo by-products themselves. U.HOF is the heavy product derived after subjecting the heavy oxo by-products to cracking which may be achieved by subjecting the by-product to a temperature in the range 300°-350° C., at low pressure and in the presence of steam and a catalyst, such as alumina.

The primary differences between the present invention and the method disclosed in the DeMunck et al. patent are: (1) DeMunck et al. include the additional steps of converting the crude oxo product into a water soluble sodium cobalt carbonyl at high temperature and high pressure by thoroughly mixing the crude oxo product with a dilute caustic solution (i.e., the caustic step), and separating the cooled and depressurized sodium cobalt carbonyl from the organic oxo products; (2) DeMunck et al. also feeds a sodium cobalt carbonyl water stream which is acidified with $H_2SO_4$ (i.e., an organic-free water stream) to the stripper reactor whereas the present invention feeds the crude oxo product directly to the stripper reactor; and (3) the process according to DeMunck et al. involves the stripping of $HCo(CO)_4$ from a water stream only such that paraffin build-up is not a major problem, whereas paraffin build-up is a major problem in Cobalt Flash processes.

The present invention also provides many additional advantages which shall become apparent as described below.

SUMMARY OF THE INVENTION

An olefin of a heavier molecular weight than the feed olefin in a hydroformylation reaction process is used as an absorbent for recovering hydro cobalt carbonyl stripped from an oxonation reactor product. The cobalt in the stripping gas is completely absorbed but light hydrocarbons, e.g., hydrocarbons having a carbon number of $C_7$ or less, are only partially absorbed, thus permitting hydro cobalt carbonyl to be recycled to the oxonation reactor without a continuing concentration build up of light hydrocarbons, e.g., paraffins.

Therefore, it is an object of the present invention to provide a method for removing cobalt values from the crude product of a cobalt-catalyzed hydroformylation reaction formed from an olefinic feedstock. The crude product typically contains cobalt compounds in addition to the organic hydroformylation reaction product. This method comprises the steps of: (a) contacting the crude product with water and an organic acid; (b) contacting the product of step (a) with a stream of stripping gas to entrain volatile cobalt compounds and light hydrocarbons in the stripping gas, whereby the entrained volatile cobalt compounds are take out overhead and organic hydroformylation reaction products and water containing water soluble cobaltous salts dissolved therein are taken out as bottoms; (c) separating the water containing water soluble cobaltous salt of step (b) from the organic hydroformylation reaction products; (d) diverting the organic hydroformylation reaction product of step (c) for further downstream treatment such as hydrogenation and/or distillation; and (e) contacting the volatile cobalt compounds from step (b) with an olefinic absorbent having a molecular weight greater than the olefinic feedstock, whereby the volatile cobalt compounds are absorbed into the olefinic absorbent, and the stripping gas and the light hydrocarbons are taken overhead as a gaseous product.

This method may further comprise the following steps in order to purge the light hydrocarbons: compressing the gaseous product from step (e); cooling the compressed gaseous product; condensing the gaseous product wherein the liquid phase comprises said light hydrocarbons and the gaseous phase comprises said stripping gas; recycling said stripping gas to step (b); and diverting said light hydrocarbon liquid for further downstream disposition.

The following additional steps may also be incorporated therewith: concentrating the water containing water soluble cobaltous salt from step (c) thereby producing a concentrated aqueous solution of cobaltous salt and a substantially cobalt-free water containing the organic acid, whereby the concentrated aqueous solution of cobaltous salt is separated from the substantially cobalt-free water containing the organic acid; recycling the substantially cobalt-free water containing the organic acid to step (b); contacting the concentrated aqueous solution of cobaltous salt with an alcohol stream, an oxonation product and/or a hydrogenation product and synthesis gas, and passing this mixture to a preformer reactor where the concentrated aqueous solution of cobaltous salt is converted to a cobalt carbonyl; and recycling the cobalt carbonyl to step (a).

This method may also include a demetalling step, i.e., contacting the water containing water soluble cobaltous salt of step (c) prior to the concentration step with a stream of oxygen-containing gas, an organic acid and water thereby producing a water soluble cobaltous salt aqueous product.

It is a further object of the present invention to provide a method for producing higher aldehydes and higher alcohols. This method includes the steps of: hydroformylating an olefinic feedstock with synthesis gas in the presence of a cobalt-containing catalyst to form a crude product containing higher aldehydes, higher alcohols, secondary products and dissolved cobalt catalysts; removing the cobalt catalysts from the crude product by cobalt flashing method wherein the volatile cobalt compounds in the absorption tower are contacted with an olefinic absorbent having a molecular weight greater than the olefinic feedstock, whereby the volatile cobalt compounds are absorbed into the olefinic absorbent and the stripping gas and the light hydrocarbons are taken overhead as a gaseous product; and recycling the contacted liquid olefinic absorbent to the hydroformylation step. Preferably, the contacted olefinic absorbent is mixed with fresh olefinic feedstock prior to recycling to the hydroformylation step.

This method for producing higher aldehydes and higher alcohols may further comprise the steps of: hydrogenating the organic hydroformylation reaction product to form a crude hydrogenated product comprising higher alcohols, light hydrocarbons, and heavy olefins; separating the higher alcohols and heavy olefins from the light hydrocarbons, whereby the higher alcohols and heavy olefins are taken out as bottoms and the light hydrocarbons are taken overhead as a light hydrocarbon product; and separating the higher alcohols from the heavy olefins and heavy by-products, whereby the higher alcohols are taken overhead as a hydrogenation product and the heavy olefins and heavy by-products are taken out as bottoms.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
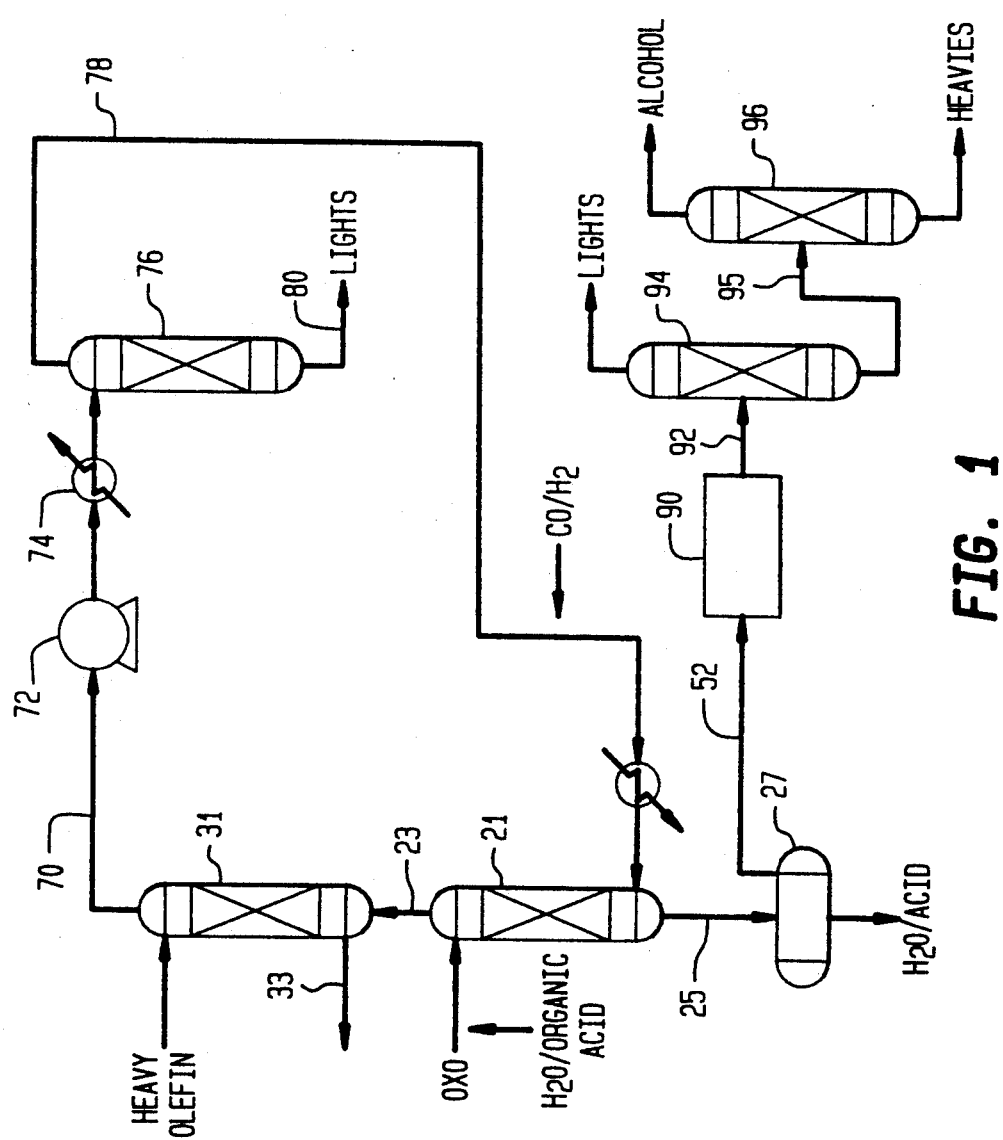
FIG. 1 is a schematic representation of the absorber, stripper, hydrogenation and distillation sections embodying the process in accordance with the present invention.

The present invention relates to the recovery of hydro cobalt carbonyl (i.e., $HCo(CO)_4$) stripped from an oxonation reactor product or higher alcohol using a heavier molecular weight higher olefin absorbent than the oxonation feed olefin itself. Using this method, hydro cobalt carbonyl is completely absorbed by the heavy olefin absorbent, while the undesirable light hydrocarbons, i.e., hexanes, pentanes or lighter, are only partially absorbed. As such, the hydro cobalt carbonyl can be recycled to the oxonation reactors avoiding an undue build up of light hydrocarbons such as paraffins within the hydroformylation system.

The hydroformylation process involves the preparation of oxygenated compounds by the reaction of carbon monoxide and hydrogen (i.e., syn gas) with olefins. The desired end product is normally higher alcohols. Typical feedstocks are $C_4$–$C_{16}$ olefins which produce $C_5$–$C_{17}$ higher alcohols. The olefin feedstock reacts to form aldehydes, alcohols, formate esters and some higher boiling condensation, esterification, and dehydration by-products. Some of the olefin feed is also hydrogenated to form paraffins.

The present invention is directed to a unique process which permits the use of the Cobalt Flash method for removing cobalt from the cobalt-catalyzed hydroformylation reaction product which utilizes olefin feedstocks having a carbon number of $C_7$ or lower. The Cobalt Flash method is described in U.S. Pat. No. 4,625,067 (Hanin) which involves the direct stripping of the hydro cobalt tetracarbonyl at low pressures using a stripping gas followed by subsequent absorption of the cobalt into the feed olefin. U.S. Pat. No. 4,625,067 is incorporated herein by reference.

This invention replaces the oxonation feed higher olefin in the absorber tower with a heavier molecular weight higher olefin to serve as the absorbent. For example, a conventional oxonation olefinic feedstock such as pentene could be replaced with a tetramer olefin absorbent, i.e., an olefin having a carbon number of 12. Slightly lighter (i.e., $C_{10}$-$C_{11}$) or slightly heavier olefinic absorbents could also be used provided that their boiling points or the boiling points of any of their reaction products do not overlap with the lighter hydrocarbons entrained together with the stripping gas and cobalt carbonyl during product fractionation.

Moreover, the present invention introduces the heavier higher olefin at a much lower feed rate than was possible with conventional olefinic feedstocks, e.g., at 10-15% of the oxonation feed rate and at a higher temperature (e.g., about 55° C. to about 85° C., if desired. This heavier higher olefin exhibits a cobalt absorption capacity of about 2 wt % or higher. This accomplishes two things, i.e., (1) the total amount of paraffin which can be absorbed will be smaller, and (2) the higher gas to olefin ratio will heat up the olefin as it is countercurrently contacted also decreasing the total amount of paraffin which is absorbed by heat of absorption of any light hydrocarbons or by sensible heat of the stripper reactor overhead gas which is typically between 48°-60° C., and accelerating the complexation of the cobalt with heavier olefin absorbent as the temperature increases. This is because the heavy olefin absorbent is much heavier than the undesirable paraffin. The heavier higher olefin temperature typically would increase by 15°-28° C. across the absorber dependent upon the amount of paraffin absorbed and the temperature and quantity of the entering stripping gas. A majority of the light hydrocarbons remain in the gas stream and exit the absorber. This gas is then compressed, cooled, and condensed such that light hydrocarbon liquid is separated from the stripping gas and diverted for fuels disposition. The stripping gas is then routed to the stripper reactor where it is reused to strip cobalt from the oxonation product.

After exiting the absorber tower the cobalt loaded heavy higher olefin is mixed with the lighter oxonation feed olefin and after addition of syn gas sent to the oxonation reactors. The hydroformylation reaction proceeds without any change from the normal operation. Only a small portion (=10-20%) of the heavy higher olefin reacts at the cobalt concentrations and temperatures employed for $C_4$-$C_7$ feedstocks which will be utilized by this invention.

The heavier olefin, paraffin, and any aldehydes, alcohols, or heavy by-products will be sent to hydrogenation and thereafter through a series of distillation columns where the heavier olefin exits the process as a heavy bottoms product, while the light hydrocarbons exit overhead in a first distillation column, and the aldehydes and alcohols are taken overhead in a second distillation column as hydrogenation products. The heavy olefin or its products can be sent on to fuels disposition or recovered in downstream fractionation facilities if economically justified.

Figure 2:
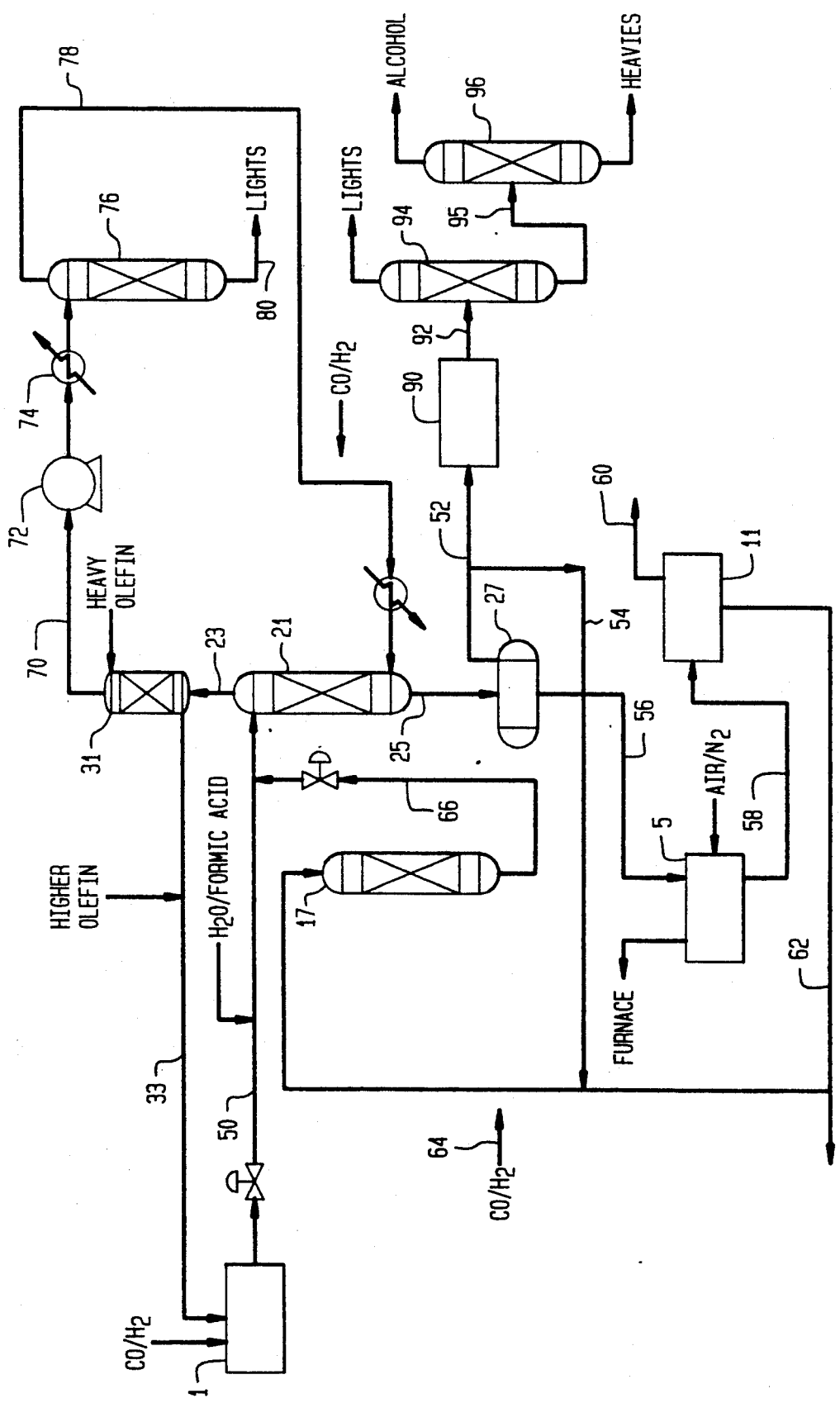
FIG. 2 is a flow diagram of a hydroformylation reaction system embodying the process of the present invention which is capable of removing cobalt values from crude products formed from an olefinic feedstock having a carbon number in the range from about $C_4$ to $C_{14}$.

The invention may be better understood by reference to the drawings, wherein FIGS. 1 and 2 illustrate a method for removing cobalt values from olefinic feedstocks having a carbon number about $C_4$ to about $C_{14}$ by using an olefin absorbent which has a heavier molecular weight than the olefinic feedstock.

As demonstrated in FIG. 2, olefinic feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 50 where it is contacted with water and an organic acid, such as formic acid. The treated crude product is thereafter contacted with a stream of stripping gas in stripper reactor 21. The stripping typically occurs at a temperature of not greater than 100° C. and at a pressure below 10 atmospheres, the pressure being lower than the decomposition pressure of the cobalt compounds at the contacting temperature, to entrain volatile cobalt compounds in the stripping gas, whereby the entrained volatile cobalt compounds are taken out overhead via conduit 23 and organic hydroformylation reaction products and water containing water soluble cobaltous salts dissolved therein are taken as bottoms via conduit 25. Also entrained within the stripping gas is certain light hydrocarbons which are more volatile than the hydro cobalt carbonyl. The stripping gas, volatile cobalt carbonyl and volatile light hydrocarbons are all carried from stripper reactor 21 via conduit 23 to absorber 31.

To avoid absorption of the volatile light hydrocarbons into the olefinic feedstock, the present invention has been modified such that instead of using the olefinic feed as the absorbent, an olefin having a heavier molecular weight than the feed olefin is used as the absorbent. The volatile cobalt in the gas is completely absorbed by the heavy olefin absorbent, while the volatile light hydrocarbons are only partially absorbed, thus permitting the hydro cobalt carbonyl to be recycled to the oxonation reactor without causing a decrease in the net olefin feed rate. Thus, the hydro cobalt carbonyl and heavy olefin absorbent are thereafter mixed with fresh olefinic feedstock and recycled to oxonation reactor 1 via conduit 33.

The gaseous products in absorber tower 31, i.e., stripper gas and a substantial portion of the lighter hydrocarbons, are taken overhead via conduit 70 where they are compressed by compressor means 72 and then condensed by cooler means 74 and knockout drum or separator 76. The condensing by cooler means 74 and separator 76 creates a liquid phase of light hydrocarbons and a gaseous phase of stripping gas. The stripping gas is then recycled to the bottom of stripper reactor 21 via conduit 78, while the light hydrocarbon liquid (i.e., lights) is diverted from the hydroformylation system for downstream fuels disposition via conduit 80.

The water phase containing soluble cobaltous salts is then separated from the organic hydroformylation reaction products by means of settling tank 27. The organic hydroformylation reaction product and heavy olefin are then carried via conduit 52 for further downstream treatment such as hydrogenation and/or distillation. In accordance with a preferred mode of operation it is desirable that the organic hydroformylation reaction product and heavy olefin be carried via conduit 52 to a hydrogenation reactor 90 where it is hydrogenated to form a crude hydrogenated product which comprises alcohols, residual light hydrocarbons and heavy olefins. The crude hydrogenated product is then carried via conduit 92 to a first distillation column 94 wherein the light hydrocarbons are taken overhead and the heavy olefins and alcohols are taken as a bottoms. The heavy olefins and alcohols are then sent to a second distillation column 96 via conduit 95 wherein the alcohols are taken overhead and the heavy olefins and heavy by-products are taken as bottoms. The heavy olefins may optionally be recycled to absorption tower 31 for use as an absorbent.

Optionally, a portion of the organic hydroformylation product may be diverted from conduit 52 via conduit 54 and recycled to preformer reactor 17. The water phase containing soluble cobaltous salts is carried via conduit 56 to settling tank or demetalling drum 5 where it is contacted with a stream of oxygen-containing gas, an organic acid and water to convert any trace levels of cobalt carbonyl, thereby producing a water soluble cobaltous salt aqueous product. The water soluble cobaltous salt aqueous product is completely free of cobalt carbonyls prior to being sent to evaporator 11. Thereafter, the water soluble cobaltous salt aqueous product is carried via conduit 58 to evaporator 11 which forms a concentrated aqueous solution of cobaltous salt and a substantially cobalt-free water containing the organic acid. The concentrated aqueous solution of cobaltous salt is then separated from the substantially cobalt-free water containing the organic acid, whereby the substantially cobalt-free water containing the organic acid is recycled via conduit 60 to stripper reactor 21, diverted to the optional water wash treatment step, or diverted to hydrogenation. The concentrated aqueous solution of cobaltous salt is carried via conduit 62 either to preformer reactor 17 or recycled to oxo reactor 1. However, prior to being fed to preformer reactor 17, the concentrated cobaltous salt is contacted with an alcohol stream, a cobalt-free organic hydroformylation reaction product, or a hydrogenation product delivered via conduit 54 and syn gas which is delivered via conduit 64. This mixture is then passed on to preformer reactor 17 where the concentrated aqueous solution of cobaltous salt is converted to a cobalt carbonyl. The cobalt carbonyl is then carried via conduits 66 and 50 to stripper reactor 21.

The organic acid is selected from the group consisting of: formic acid, acetic acid, propionic acid, and other acids having a boiling point approximately the same as water. The organic acid is preferably formic acid and the water soluble cobaltous salt is preferably cobalt formate.

EXAMPLE 1

To better illustrate principle of the present invention a laboratory experiment was performed to simulate production of hexyl alcohol utilizing a mixed nonene/pentane feedstock containing approximately 32% paraffin. The nonene which does not react to oxygenates in the oxonation reactor will not strip overhead in the stripper reactor due to its lower volatility and thus only the pentane and hydro cobalt carbonyl will be stripped overhead. As such, this experiment accurately simulates the situation of a pentene/pentane feedstock in which only the unreacted olefins and paraffins would be stripped with the hydro cobalt carbonyl but not the higher boiling $C_6$ oxygenates. To simulate the absorber two jacketed batch absorbers were connected in series and filled with tetramer ($C_{12}$) and heated to 65° C. Two downstream reactors connected in series were also filled with tetramer but operated at a lower temperature to capture paraffin and remaining cobalt for material balance purposes.

The nonene/pentane mixture was oxonated at 175° C. at a pressure of 300 bar with a $H_2$ to CO (i.e., syn gas) ratio of 1.2:1. The oxonation product was stripped at a pressure of 1.8 bar. The stripper reactor temperature was 95° C. The gas to liquid ratio was 130:1 with 18% water on feed. The free formic acid level in the stripper bottoms was 2.5 weight %.

The first two absorbers were operated at 65° C. and at a pressure of 1.8 bar. Following the two lead absorbers were two additional absorbers also in series and filled with tetramer which operated at 20° C. The run was conducted for 90 hours. By measuring the pentane concentration in the first two and final two absorbers a steady state distribution coefficient of the pentane between the syn gas and the tetramer at 65° C. and 20° C., respectively, was observed. The steady state pentane level in the two lead absorbers was 7 weight % on total absorber liquid at 65° C. which results in a distribution coefficient of 0.804 mole % pentane in gas per mole % pentane in the absorber liquid. The pentane level in the last two absorbers operating at 20° C. was 19 wt % on total absorber liquid resulting in a distribution coefficient of 0.266 mole % pentane in gas per mole % pentane in absorber liquid. Of the cobalt stripped overhead, 88.7 wt % was absorbed by the two lead batch absorbers. While the experiment lasted for 90 hours to attempt to saturate the tetramer to its approximate 2.5 wt % cobalt limit this was not achieved. Due to a combination of time and higher temperature some of the cobalt converted to dicobalt octacarbonyl (i.e., $CO_2(CO)_8$) which precipitated. This will not be a concern in a commercial application since absorber residence times are normally only a few minutes. However, if the solution is to be stored it should probably be cooled to prevent any precipitation.

This experiment clearly demonstrates that by operating the absorbers at elevated temperature good cobalt absorption can be achieved using a small amount of heavy higher olefin (i.e., 10% of oxonation olefin feed) with a minimum of pentane absorption but as temperature is lowered to more conventional levels the pentane absorbed becomes excessive and would seriously limit oxonation net feed rates. This effect would become more serious before steady state was achieved.

EXAMPLE 2

The same experiment as discussed in Example 1 above was repeated at similar conditions except that the olefinic feed was iso hexene with hexane, i.e., the hydroformylation product contained 31.6 wt % hexane. Tetramer was again used in the absorbers with the two lead absorbers operating at 82° C. and the final two absorbers at 20° C. At steady conditions the two lead absorbers operating at 82° C. contained 11.9 wt % hexane based upon total absorber liquid which translated into a distribution coefficient of 0.59 mole % hexane in gas per mole % hexane in the absorber liquid. The absorbers operating at 20° C. contained 51.7 wt % hexane which translates into a distribution coefficient of 0.041 mole % hexane in gas per mole % hexane in the absorber liquid. This experiment lasted for 18 hours and, as in Example 1, a portion of the absorbed $HCo(CO)_4$ reacted to form dicobalt octacarbonyl $(Co_2(CO)_8)$ which precipitated as crystals owing to the elevated temperatures illustrating the need for either short contact times and/or cooling prior to storage in a commercial application.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A method for removing cobalt values from the crude product of a cobalt-catalyzed hydroformylation reaction formed from an olefinic feedstock, said crude product containing cobalt compounds in addition to an organic hydroformylation reaction product, which comprises:
    a. contacting said crude product with water and an organic acid selected from the group consisting of: formic acid, acetic acid, propionic acid, and acids having a boiling point approximately the same as water;
    b. contacting the product of step (a) with a stream of stripping gas to entrain volatile cobalt compounds and light hydrocarbons in said stripping gas, whereby said entrained volatile cobalt compounds are taken out overhead and organic hydroformylation reaction products and water containing water soluble cobaltous salts dissolved therein are taken out as bottoms;
    c. separating said water containing water soluble cobaltous salt of step (b) from said organic hydroformylation reaction products;
    d. diverting said organic hydroformylation reaction product of step (c) for further downstream treatment by at least one method selected from the group consisting of: hydrogenation and distillation; and
    e. contacting said volatile cobalt compounds from step (b) with an olefinic absorbent having a molecular weight greater than said olefinic feedstock, whereby said volatile cobalt compounds are absorbed into said olefinic absorbent, and said stripping gas and said light hydrocarbons are taken overhead as a gaseous product.

2. The method according to claim 1 further comprising the steps of:
    compressing the gaseous product from step (e);
    cooling the compressed gaseous product;
    condensing the gaseous product to form a liquid phase comprising said light hydrocarbons and a gaseous phase comprising said stripping gas;
    recycling said stripping gas to step (b); and
    diverting said light hydrocarbon liquid for further downstream disposition.

3. The method according to claim 1 wherein said olefinic feedstock has a carbon number in the range between about $C_4$ to about $C_7$ and said olefinic absorbent has a carbon number of about $C_{10}$ to about $C_{14}$.

4. The method according to claim 1 wherein the contacting in step (e) occurs at a temperature in the range between about 55° C. to about 85° C.

5. The method according to claim 1 further comprising the steps of:
    concentrating the water containing water soluble cobaltous salt from step (c) thereby producing a concentrated aqueous solution of cobaltous salt and a substantially cobalt-free water containing said organic acid, whereby said concentrated aqueous solution of cobaltous salt is separated from said substantially cobalt-free water containing said organic acid;
    recycling said substantially cobalt-free water containing said organic acid to step (b);
    contacting said concentrated aqueous solution of cobaltous salt with synthesis gas and at least one of the following: an alcohol stream and an aldehyde stream, and passing this mixture to a preformer reactor where said concentrated aqueous solution of cobaltous salt is converted to a cobalt carbonyl; and
    recycling said cobalt carbonyl to step (a).

6. The method according to claim 5 further comprising the step of:
    contacting said water containing water soluble cobaltous salt of step (c) prior to said concentration step with a stream of oxygen-containing gas, an organic acid and water thereby producing a water soluble cobaltous salt aqueous product.

7. The method according to claim 1 wherein said organic acid is formic acid and the resultant cobaltous salt is cobalt formate.

8. The method according to claim 5 wherein the concentrating step occurs in either a flash unit or evaporator.

9. The method according to claim 5 wherein the concentrated aqueous solution of cobaltous salt is converted to a cobalt carbonyl in the presence of a noble metal catalyst disposed within said preformer reactor.

10. The method according to claim 9 wherein said noble metal catalyst is gold, platinum or palladium.

11. The method according to claim 10 wherein said concentrated aqueous solution of cobaltous salt is converted to a cobalt carbonyl by contacting of phases at a pressure in the range between about 103.42 bar to about 310.27 bar and a temperature in the range between about 100° C. to about 150° C.

12. The method according to claim 1 wherein said organic hydroformylation reaction products of step (d) are subjected to a water wash treatment to remove residual cobalt values remaining therein prior to further downstream treatment by hydrogenation and/or distillation.

13. The method according to claim 12 wherein the wash water from said water wash treatment is recycled to step (a).

14. A method for producing higher aldehydes and higher alcohols which comprises:

hydroformylating an olefinic feedstock with synthesis gas in the presence of a cobalt-containing catalyst to form a crude product containing higher aldehydes, higher alcohols, secondary products and dissolved cobalt catalysts;

removing said cobalt catalysts from said crude product by the following steps: (a) contacting said crude product with water and an organic acid selected from the group consisting of: formic acid, acetic acid, propionic acid, and acids having a boiling point approximately the same as water; (b) contacting the product of step (a) with a stream of stripping gas to entrain volatile cobalt compounds in said stripping gas, whereby said entrained volatile cobalt compounds and light hydrocarbons are take out overhead together with said stripping gas and organic hydroformylation reaction products and water containing water soluble cobaltous salts dissolved therein are taken out as bottoms; (c) separating said water containing water soluble cobaltous salt of step (b) from said organic hydroformylation reaction products; (d) diverting said organic hydroformylation reaction product of step (c) for further downstream treatment by at least one method selected from the group consisting of: hydrogenation and distillation; and (e) contacting said volatile cobalt compounds from step (b) with an olefinic absorbent having a molecular weight greater than said olefinic feedstock, whereby said volatile cobalt compounds are absorbed into said olefinic absorbent and said stripping gas an said light hydrocarbons are taken overhead as a gaseous product; and recycling said contacted liquid olefinic absorbent from step (e) to said hydroformylation step.

15. The method according to claim 15 further comprising the steps of:

compressing the gaseous product from step (e);
cooling the compressed gaseous product;
condensing the gaseous product to form a liquid phase comprising said light hydrocarbons and a gaseous phase comprising said stripping gas;
recycling said stripping gas to step (b); and
diverting said light hydrocarbon liquid for further downstream disposition.

16. The method according to claim 14 wherein said contacted olefinic absorbent is mixed with fresh olefinic feedstock prior to recycling to said hydroformylation step.

17. The method according to claim 14 further comprising the steps of:

hydrogenating said organic hydroformylation reaction product of step (d) with hydrogen in the presence of a catalyst to form a crude hydrogenated product comprising higher alcohols, light hydrocarbons, and heavy olefins; and separating said heavy olefins from said higher alcohols and light hydrocarbons, whereby said heavy olefins are taken out as bottoms and said higher alcohols and light hydrocarbons are taken overhead as a gaseous hydrogenation product.

18. The method according to claim 14 wherein said olefinic feedstock has a carbon number in the range between about $C_4$ to about $C_7$ and said olefinic absorbent has a carbon number of about $C_{10}$ to about $C_{14}$.

19. The method according to claim 14 wherein the contacting in step (e) occurs at a temperature in the range between about 55° C. to about 85° C.

20. The method according to claim 14 further comprising the steps of:

concentrating the water containing water soluble cobaltous salt from step (c) thereby producing a concentrated aqueous solution of cobaltous salt and a substantially cobalt-free water containing said organic acid, whereby said concentrated aqueous solution of cobaltous salt is separated from said substantially cobalt-free water containing said organic acid;

recycling said substantially cobalt-free water containing said organic acid to step (b);

contacting said concentrated aqueous solution of cobaltous salt with synthesis gas and at least one of the following: an alcohol stream and an aldehyde stream, and passing this mixture to a preformer reactor where said concentrated aqueous solution of cobaltous salt is converted to a cobalt carbonyl; and recycling said cobalt carbonyl to step (a).

21. The method according to claim 20 further comprising the step of:

contacting said water containing water soluble cobaltous salt of step (c) prior to said concentration step with a stream of oxygen-containing gas, said organic acid and water thereby producing a water soluble cobaltous salt aqueous product.

* * * * *